United States Patent [19]

Brantman

[11] Patent Number: 4,687,782

[45] Date of Patent: Aug. 18, 1987

[54] NUTRITIONAL COMPOSITION FOR ENHANCING SKELETAL MUSCLE ADAPTATION TO EXERCISE TRAINING

[75] Inventor: Eugene R. Brantman, Richardson, Tex.

[73] Assignee: Nutri-Fuels Systems, Inc., Garland, Tex.

[21] Appl. No.: 680,161

[22] Filed: Dec. 10, 1984

[51] Int. Cl.$^4$ ................. A61U 31/195; A61K 31/195
[52] U.S. Cl. .................................... 514/561; 514/562; 514/567
[58] Field of Search .................. 514/561, 562, 567

[56] References Cited

U.S. PATENT DOCUMENTS

| | | | |
|---|---|---|---|
| 3,832,465 | 8/1974 | Ghadimi | 424/177 |
| 3,950,529 | 4/1976 | Fischer | 424/273 |
| 4,357,343 | 11/1982 | Madsen | 424/274 |
| 4,438,144 | 3/1984 | Blackburn | 424/319 |

OTHER PUBLICATIONS

Hong, S. and D. Layman, "Effects of Leucine on In Vitro Protein Synthesis", *J. Nutr.*, 114: 1204–1212; 1984.

Felig, P. and Wahren, J., "Fuel Homeostasis in Exercise"; *New England J. Med.*, 293: 1078–1084; 1975.

White, T. and Brooks, G., "Amino Acid and Glucose Oxidation"; *Med. Sci. Sports*, 9: 67; date unknown.

Ahlborg, G. et al, "Splanehnic and Leg Metabolism of Glucose, Free Fatty Acids and Amino Acids", *Journal of Clinical Investigations*, 53:1080–1090; 1974.

Milward, D. et al, "Effect of Exercise on Protein Metabolism as Explored with Stable Isotopes"; *Fed. Proc.*, 41: 2686–2691; 1982.

Buono, M. et al, "Blood Lactate and Ammonium Ion Accumulation During Graded Exercise in Humans"; *J. Appl. Physiology*, 57: 135–139; 1984.

Parkhouse, W. et al, "Possible Contribution of Skeletal Muscle Buffers to Enhanced Anerobic Performance"; *Med. and Sci. in Sports and Exer.*, vol. 16, No. 4, pp. 326–338; 1984.

Fruend, H. et al, "Amino Acid Derangements in Patients with Sepsis"; *Ann. Surg.*, 188: 423–430; 1978.

Askew, E. et al, "Urinary Carnitine Excretion Patterns During Seven Days Exercise Training in Men"; *Fed. Proc.*, 43: 617; 1984.

May, M. et al, "Mechanism of the Stimulation of Branched Chain Oxoacid Oxidation in Liver by Carnitine"; *J. Biol. Chem.*, 255: 8394–8397; 1980.

Bohles, M. et al, "The Effect of L–Carnitine–Supplemented Total Parenteral Nutrition on Tissue Amino Acid Concentrations"; *J. Nutr.*, 114: 671–676; 1984.

Kosolcharoen, P. et al, "Improved Exercise Tolerance After Administration of Carnitine"; *Current Therapeutic Research*, 30: 753–764; 1981.

Stewart, J. et al, "Effects of Branched Chain Amino Acids on Spontaneous Growth Hormone Secretion"; *Endocrinology*, 115: 1897–1900; 1984.

O'Connor, J. et al, "Protective Effect of L–Carnitine on Hyperaminoemia"; *Fed. European Bio. Soc. Ltrs.*, 166: 331–334.

Wagenmakers, A. et al, "Effect of Starvation and Exercise on Actual and Total Activity of Branched–Chain 2–Oxo Acid Dehydrogenase Complex"; *Biochem. J.*, 223:815–821; 1984.

Mortimore, G. et al, "Lysosonal Pathways in Hetatic Protein Degradation: Regulatory Role of Amino Acids"; *Fed. Proc.*, 43: 1289–1294; 1984.

*Primary Examiner*—Stanley J. Friedman
*Attorney, Agent, or Firm*—Richards, Harris, Medlock & Andrews

[57] ABSTRACT

A combination of amino acids (carnitine, glutamine, isoleucine, leucine and valine) provide diet supplements which employ branched amino acids (BAA) to promote muscle adaptation to strenuous exercise. The diet supplements provide the BAA substrate which is utilized at the expense of muscle mass as well as liver protein, stimulate muscle and liver protein synthesis, contribute amino groups for the synthesis of alanine and glutamine, encourage metabolism of pyruvate to alanine, rather than to lactate, and encourage proton efflux from muscle (via glutamine).

24 Claims, 1 Drawing Figure

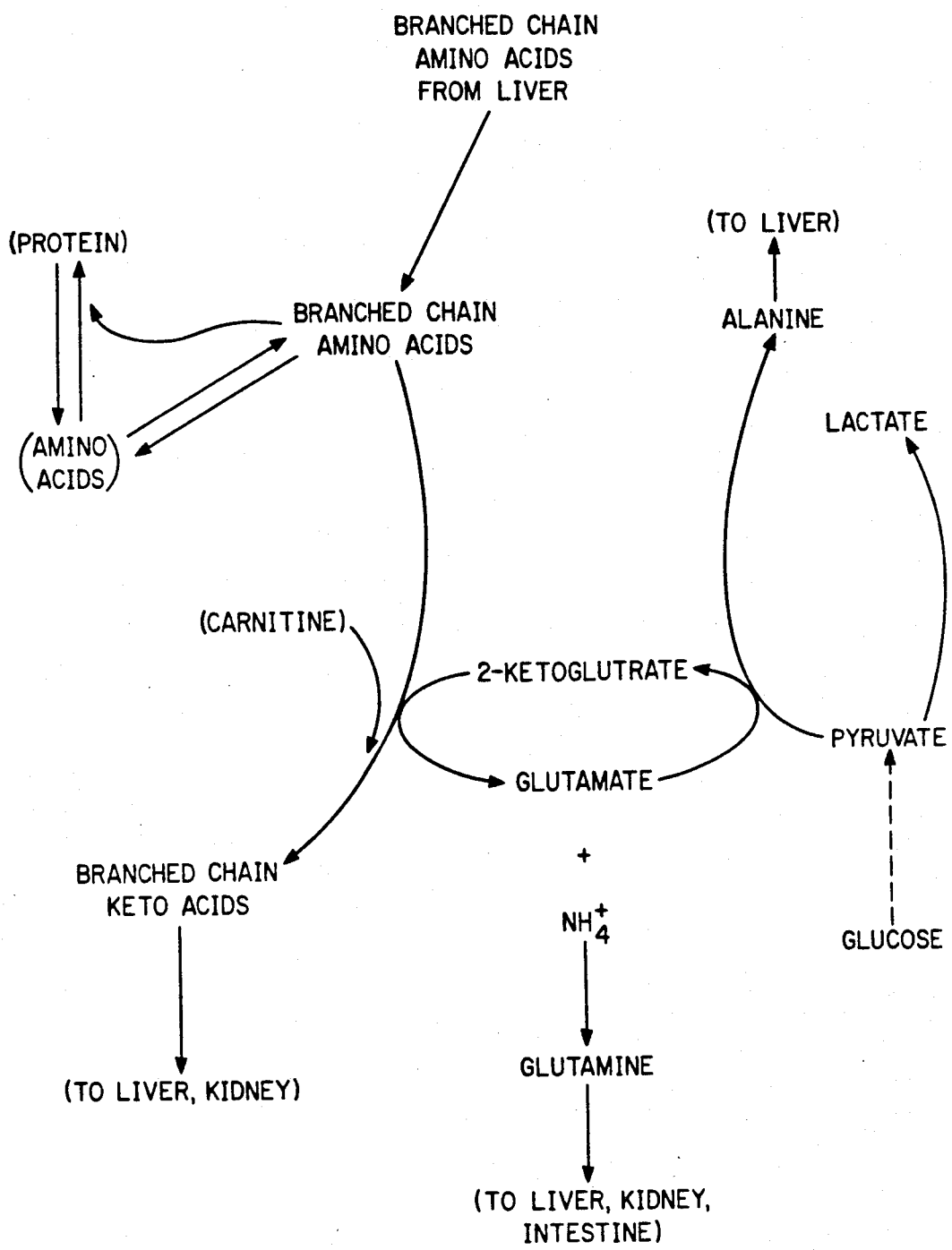
INTERRELATIONSHIPS OF PROTEIN AND AMINO ACIDS
WITHIN MUSCLE CELLS

NUTRITIONAL COMPOSITION FOR ENHANCING SKELETAL MUSCLE ADAPTATION TO EXERCISE TRAINING

BACKGROUND OF THE INVENTION

1. Field of the Invention:

This invention relates to compositions of specific nutrients to facilitate the adapation of skeletal muscle to programs of strenuous exercise. In particular, the invention is directed to novel combinations of certain amino acids which exert beneficial effects on the metabolism (especially protein synthesis) of skeletal muscle. The specific field of application of these amino acids is in exercise training, with a training diet providing:

1. an improved, novel mixture of certain nutrients to maximize protein synthesis in skeletal muscle; and
2. nutrients to "spare" the liver which is metabolically stressed on behalf of skeletal muscle as a result of exercise.

2. Description of the Prior Art:

Athletes who participate in sports at any level—amateur or professional—strive to bring their bodies to a physical state which is optimal for the sport or activity of interest. One factor which enables athletes to participate effectively is a high degree of development of the aerobic capacity and/or strength of skeletal muscle.

Both aerobic capacity and strength—especially the latter—is a function of training and of muscle mass. These in turn require net synthesis of proteins in the muscle. Strenuous exercise is an effective stimulus for protein synthesis. However, muscle requires a large array of nutrients, including amino acids (which are derived from protein) for protein synthesis. These nutrient substrates can be supplied by ingesting diets which provide the necessary amounts of protein (the source of amino acids), calories and other nutrients.

The desire to attain, in a rapid manner, the maximum degree of skeletal muscle adaptation to exercise has led some athletes to resort to the use of drugs. Such drugs, particularly steroids, are known to "force" muscle growth (protein synthesis) to degrees greater than can be achieved by exercise and diet alone. The use of such drugs is both illegal and dangerous.

Thus, it is desirable to apply training programs which employ a combination of specific exercise technique and diet. This is the only known and accepted manner for stimulation of the protein synthesis required for skeletal muscle adaptation. Many nutrients must be supplemented to athletes in training. This invention is directed at specific amino acids to be supplemented to such training diets.

Nearly all amino acids, both essential (indispensible) and non-essential (dispensible) are required by cells as substrates (i.e., raw materials) for protein synthesis. However, the critical feature of this invention is the specific application of certain amino acids (carnitine, glutamine, isoleucine, leucine and valine), which are known to exert net stimulatory effects on protein synthesis in skeletal muscle and liver.

Nine amino acids are known to be essential nutrients in the diet of healthy adults. Three of these essential amino acids are isoleucine, leucine and valine; they are termed the "branched amino acids" or "branched-chain amino acids" (BAA) because they share a specific type of chemical structure. For over a decade the BAA—and leucine in particular—have been known to stimulate protein synthesis in at least some skeletal muscles. The BAA produce this effect in liver as well.

The relationship between the BAA and skeletal muscle is even more intimate, a fact which is significant to this invention. Certain metabolic reactions involving the BAA occur in many organs. Since skeletal muscle mass in toto is greater than any other organ, the reactions of BAA in muscle are thus of quantitative significance.

It is well known that skeletal muscle is the primary site for the initial step in the catabolism of the BAA. Catabolism is the metabolic breaking down of the BAA resulting in energy production, and is often termed "oxidation" or "burning".

The first metabolic reaction in oxidative catabolism of BAA is "transamination" (enzymatic transfer of the alpha-amino group to another molecule) resulting in the formation of a branched keto acid (BKA) and a different amino acid (see FIGURE). The BKA can either accept an amino group, thus becoming a BAA again; or be further and irreversibly catabolized for calories. The BKA are so catabolized to a lesser extent within muscle cells. The major quantity of BKA is exported from muscle via the blood to other organs (such as liver and kidney) where they are catabolized or re-aminated.

It is well known that strenuous exercise increases the oxidation ("burning") of BAA. In fact, it has been shown that trained muscle, while in the resting (non-exercising state), also oxidizes more BAA than non-trained muscle. Further, it has been shown that the BAA burned by skeletal muscle during exercise is derived from muscle protein which is degraded during exercise, as well as from BAA delivered to the muscle in the bloodstream. The major source, during exercise, of the blood-borne BAA is the liver.

Thus, it is known that exercise causes transient periods (which extend beyond the actual exercise) wherein the normal balance in skeletal muscle of protein synthesis and degradation has been tipped toward a net, or relative, increase in protein degradation. That is, strenuous exercise cuases muscle to burn up a portion of its protein structure.

The reason for this increased "burning" of protein, especially BAA, is not clear. Some have suggested that this process reflects a "clean up" of damage caused by exercise-induced ischemia. Others suggest that increased protein oxidation contributes to the increased caloric demand of exercise. However, it has been clearly shown that the quantitative contribution of protein oxidation to the increased energy needs of exercise is quite small. Nevertheless, oxidation of BAA may be significant in view of the fact that their oxidation generates the amino acids alanine and glutamine, which can be transported from muscle to be used as fuels elsewhere. Alanine is carried, via the blood, to the liver where it contributes to the formation of glucose, the latter being the preferred fuel of the brain. Glutamine is a known fuel for the kidney and intestine. Whatever the reason, it appears that increased oxidation of protein and BAA during exercise is obligatory.

One of the functions for the oxidation of BAA in exercising muscle is, in effect, to remove lactate from muscle. It is well known that strenuously exercising muscle burns glucose in a largely anaerobic manner, resulting in the generation of lactate. (Lactate is derived directly from pyruvate.) Build up of lactate in muscle is associated with muscle fatigue, and is considered to be undesirable.

The drawing FIGURE shows that the amino groups of the BAA are transferred via intermediate reactions, to pyruvate, resulting in the formation of alanine. Alanine is exported to the liver to participate in glucose synthesis. That pyruvate which is thus involved in alanine synthesis is not converted to lactate. Therefore, BAA oxidation serves, in effect, to modulate lactate accumulation in muscle.

In addition, protons $H^+$ from catabolic reactions must be eliminated, so as to remove any risk of a drop in pH. The proton is removed from muscle by combining (in the form of ammonium—$NH^+_4$) with glutamate to form glutamine. When taken up by the kidney, $NH_4^{30}$ (and hence $H^+$) is removed and excreted via the acid urine.

SUMMARY OF THE INVENTION

In summary, the object of the present invention is to provide diet supplements which comprise BAA (and other amino acids as discussed below) in order to promote muscle adaptation (to strenuous exercise) via the following mechanisms:

1. to "spare" muscle protein and especially muscle BAA by providing the very substrate which is being utilized at the expense of muscle mass as well as of liver protein.
2. to stimulate muscle and liver protein synthesis, which is a function of at least leucine, apart from the role of BAA as substrates for protein synthesis.
3. to contribute amino groups for the synthesis of alanine and glutamine, both of which are involved in gluconeogenesis.
4. to encourage metabolism of pyruvate to alanine, rather than to lactate.
5. to encourage proton efflux from muscle (via glutamine), so as to maintain intramuscular pH at optimum.

A further observation concerns the BAA and the liver. It is known that during strenuous exercise in man the liver suffers a net loss of the BAA; the skeletal muscle concomitantly takes up BAA from the blood. Thus, the increased burning of BAA in muscle seems to cause a "drain" on the BAA stored in liver protein. Further, it has been noted that the rate of protein breakdown in the liver can be partly reversed by amino acids—in particular glutamine. In particular, it was noted that an increased amount of glutamine ws exported from the liver during exercise, which may be related to the effect of this amino acid on protein synthesis. Glutamine is, therefore, included in this invention, to provide the liver with that amino acid which is known to encourage protein synthesis, in the proper metabolic environment. The liver, being central to numerous metabolic functions, may in fact be the key to adaptation to exercise.

The last amino acid to be part of this invention is carnitine. (While not all authorities will agree with designating carnitine an amino acid, it is so designated here; its chemical designation is: 3-hydroxy-4-N-trimethylaminobutyrate.) This amino acid is synthesized in the body from two other (essential) amino acids (lysine and methionine). Carnitine is known to be required for the oxidation of fat for calories, and that fat is a major fuel for skeletal muscle during exercise.

It is known as well that carnitine metabolism increases during exercise training. Further, carnitine has been shown to protect against the toxic effects of ammonia. Ammonia is generated during catabolism of amino acids, such as occurs during strenuous exercise, and is toxic. The ready removal of ammonia from muscle is thus desirable.

It is only recently known that carnitine may be important in the oxidation of the BAA in muscle. Also, a study of patients with coronary-artery disease showed that those patients who received oral supplements of carnitine did significantly better on exercise tests.

The present invention employs carnitine to optimize skeletal muscle function in relation to oxidation of fatty acids for calories; to the oxidation of BAA for the effects summarized above; and to enhance the removal of toxic ammonia.

Heretofore, conventional diets for "sports" or for exercise programs have employed supplements of whole protein, without consideration of the possible applications of the pharmacologic properties of specific components (amino acids) of the proteins. What is needed is a dietary supplement which provides the best metabolic milieu to permit and encourage protein synthesis in skeletal muscle and in liver.

Accordingly, it is an object of this invention to supply an amino acid supplement which is directed at optimizing protein synthesis in skeletal muscle and in liver.

The objects of the invention are realized by a careful selection of specific amino acids to be added to whole protein and other nutrients, so as to achieve a diet which is enriched with specific amino acids (carnitine, glutamine, isoleucine, leucine and valine), in order to maximize protein synthesis in skeletal muscle.

BRIEF DESCRIPTION OF THE DRAWING

The sole FIGURE of the drawing is a simplified diagram which illustrates interrelationships of protein and amino acids within muscle cells.

DETAILED DESCRIPTION OF THE PREFERRED EMBODIMENTS

The compositions of this invention are defined by the following L-amino acids in the cited ranges (expressed in grams of each amino and per 100 grams of whole protein).

| Amino Acid | Grams per 100 grams whole protein |
|---|---|
| L-carnitine | from 0.3 to 2.0 |
| L-glutamine | from 10.0 to 30.0 |
| L-isoleucine | from 15.0 to 40.0 |
| L-leucine | from 20.0 to 45.0 |
| L-valine | from 15.0 to 40.0 |

The amino acids used in practicing this invention are preferably pure, and in the crystalline form. They should be in the L-form, rather than the D-form. The amino acids are preferred to be in the free form, rather than as salts or derivatives; however, the salts and derivatives may be employed if those forms enable superior formulation with other nutrients as described below. The keto- (or oxo-) forms of the amino acids may also be employed.

The composition is suitable for oral intake. Total daily intake of the supplement may vary as needed, but generally will not exceed 30% of the individual's usual protein intake. The supplement should be composed of the appropriate amino acids in conjunction with other nutrients, including whole protein, vitamins, minerals, all of which may be combined with the amino acid composition of the invention prior to administration, or supplied through ordinary dietary sources.

The ranges of the amino acid proportions recited above, the concentrations of ingested amino acid-containing diet supplements, the amount of amino acids ingested per day, and the rate of ingestion of amino acids or supplements containing them may all be varied to refine the adaptive responsiveness of the individual in training.

The effectiveness of the dietary program which utilizes these amino acid supplements may be assessed by well-known measures of aerobic training and of skeletal muscle function, during and following the exercise period. Suitable examples of functional efficacy include the following: time to onset of muscle or overall fatigue, intensity of effort, pulse rate, oxygen consumption, strength testing (by dynamometry), and mid-arm muscle circumference. Other assessment criteria will be apparent to the ordinary artisan.

The relative proportions of the amino acids are preferably within 20% of the ranges recited above. The proportions of the BAA (isoleucine, leucine and valine) should be approximately 50% (w:w) of the whole protein portion of the diet supplement.

The concentration of nutrients should be such that osmolality of the supplement, as ingested, be not greater than 400 m Osm/kg of water; this will avoid subjecting the intestine to "osmotic shock" during a period of reduced hemoperfusion. One unit of supplement would contain approximately 10% of the individual's usual daily intake of protein. Three units would be ingested in roughly the following schedule. One unit to be consumed slowly (over 10-15 minutes) beginning 45 to 30 minutes prior to the onset of strenuous exercise. A second unit to be consumed in small amounts during most of the exercise period. The third unit to be ingested slowly (over 10-15 minutes) within 30 to 60 minutes after exercise ceases.

The above manner of spreading out intake of the supplements serves two purposes: 1. it avoids intestinal distress by allowing only small volumes of fluids and nutrients to enter the intesting during exercise; and 2. it encourages a steady input of nutrients into the bloodstream during the entire "peri-exercise period" (i.e., before, during and after exercise), since this is when the nutrients will be most needed and used for their unique effects.

The invention will be more fully understood by reference to the following example.

EXAMPLE 1

This example demonstrates the formulation and use of the diet supplement which contain the AA composition of this invention.

The formulation of one unit consists of the following amounts of nutrients per 400 ml of water:

| Nutrient | Quantity |
| --- | --- |
| Amino Acids | |
| L-carnitine | 0.025 gr. |
| L-glutamine | 0.05 gr. |
| L-isoleucine | 0.625 gr. |
| L-leucine | 0.85 gr. |
| L-valine | 0.625 gr. |
| Protein | |
| Casein, soy protein, lactalbumin, or any combination thereof. | 2.5 gr. |

-continued

| Nutrient | Quantity |
| --- | --- |
| Carbohydrates | |
| Corn syrup solids; sucrose | 25.0 gr. |
| Fats | |
| Sunflower oil; soybean oil (1:1, vol.:vol.) | 5.5 gr. |
| Medium-chain triglycerides | 6.0 gr. |
| Vitamins (10% RDA) | |
| Vitamin C | 6.0 mg. |
| Folic acid | 35 microgram |
| Vitamin B1 | 1.0 mg. |
| Vitamin B2 | 1.2 mg. |
| Niacin | 1.7 mg. |
| Vitamin B6 | 0.15 mg. |
| Biotin | 15 microgram |
| Choline | 5.0 mg. |
| Vitamin B12 | 1.0 microgram |
| Pantothenate | 0.2 mg. |
| Minerals | |
| Sodium | 60 mg. |
| Magnesium | 20 mg. |
| Potassium | 200 mg. |
| Calcium | 50 mg. |
| Phosphate | 75 mg. |
| Chloride | 350 mg. |

The volume of water should be adjusted to keep the osmolality between 300 and 600 m Osm/kg, preferably towards the low end of this range.

Three supplement units are taken as described above. The total intake is carefully recorded. Depending on the exercise regime appropriate to a given sport, relevant parameters of efficacy are monitored during and following the exercise period. Dietary supplements should be dosed according to the needs of the athlete.

This invention is intended only as a supplement; the diet composition suggested should not be used as the sole or major source of nutrition on a daily basis. It should also not be ingested by individuals not undergoing exercise programs.

What is claimed is:

1. A method of supplementing the diet of a athlete, comprising the steps of: providing the athlete with a solution comprising an amino acid mixture consisting essentially of 0.025 grams L-carnitine, 0.5 grams L-glutamine, 0.625 grams L-isoleucine, 0.85 grams L-leucine and 0.625 grams L-valine mixed with 400 milliliters of water; and having the athlete drink the solution.

2. A method as set forth in claim 1, further comprising the steps of: providing the athlete with the solution that further includes 2.5 grams of proteins being one or more selected from the group consisting of casein, soy protein and lactalbumin.

3. A method as set forth in claim 1, further comprising the steps of: providing the athlete with the solution that further includes 25.0 grams of carbohydrates being one or more selected from the group consisting of syrup solids and sucrose.

4. A method as set forth in claim 1, further comprising the steps of: providing the athlete with the solution that further includes a fat mixture consisting essentially of 2.5 grams of a mixture of sunflower oil and soybean oil in a volumetric ratio of 1:1 and of 6.0 grams of medium-chain triglycerides.

5. A method as set forth in claim 1, further comprising the steps of: providing the athlete with the solution that further includes a vitamin mixture consisting essentially of 6.0 mg. of Vitamin C, 35 microgram of Folic acid, 1.0 mg. Vitamin B1, 1.2 mg. Vitamin B2, 1.7 mg. of Niacin, 0.15 mg. Vitamin B6, 15 microgram of Biotin, 5.0 mg. of Choline, 1.0 microgram of Vitamin B12 and 0.2 mg. Pantothenate.

6. A method as set forth in claim 1, further comprising the steps of: providing the athlete with the solution that further includes a mineral mixture consisting essentially of 60 mg. of Sodium, 20 mg. of Magnesium, 200 mg. of Potassium, 50 mg. of Calcium, 75 mg. of Phosphate and 350 mg. of Chloride.

7. A method as set forth in claim 1, further comprising the steps of: providing the athlete with the solution that further includes 2.5 grams of proteins being one or more selected from the group consisting of casein, soy protein and lactalbumin; 25.0 grams of carbohydrates being one or more selected from the group consisting of syrup solids and sucrose; a fat mixture consisting essentially of 2.5 grams of a mixture of sunflower oil and soybean oil in a volumetric ratio of 1:1 and of 6.0 grams of medium-chain triglycerides; a vitamin mixture consisting essentially of 6.0 mg. of Vitamin C, 35 microgram of Folic acid, 1.0 mg. Vitamin B1, 1.2 mg. Vitamin B2, 1.7 mg. of Niacin, 0.15 mg. Vitamin B6, 15 microgram of Biotin, 5.0 mg. of Choline, 1.0 microgram of Vitamin B12 and 0.2 mg. Pantothenate; and a mineral mixture consisting essentially of 60 mg. of Sodium, 20 mg. of Magnesium, 200 mg. of Potassium, 50 mg. of Calcium, 75 mg. of Phosphate and 350 mg. of Chloride.

8. A composition adapted to be used with water as a diet supplement for facilitating the adaptation of skeletal muscle and liver to a program of strenuous exercise, comprising: an amino acid mixture consisting essentially of 0.7 to 1.8 weight percent carnitine, 1.8 to 3.4 weight percent glutamine, 23.2 to 31.2 weight percent isoleucine, 50.7 to 32.4 weight percent leucine and 23.6 to 31.2 weight percent valine.

9. A composition as set forth in claim 8, further comprising: one or more proteins selected from the group consisting of casein, soy protein and lactalbumin.

10. A composition as set forth in claim 9, further comprising: the isoleucine, leucine and valine in said amino acid mixture being from 50 to 125 grams per 100 grams of said protein.

11. A composition as set forth in claim 9, further comprising: the carnitine in said amino acid mixture being from 0.3 to 2.0 per 100 grams of said protein.

12. A composition as set forth in claim 9, further comprising: the glutamine in said amino acid mixture being from 10.0 to 30.0 grams per 100 grams of said protein.

13. A composition as set forth in claim 8, further comprising: said amino acid mixture consisting essentially of L-carnitine, L-glutamine, L-isoleucine, L-leucine and L-valine.

14. A composition as set forth in claim 8, further comprising: one or more carbohydrates selected from the group consisting of syrup solids and sucrose.

15. A composition as set forth in claim 8, further comprising: one or more fats selected from the group consisting of sunflower oil, soybean oil and a medium-chain triglyceride.

16. A composition as set forth in claim 8, further comprising: one or more vitamins selected from the group consisting of Vitamin C, Folic acid, Vitamin B1, Vitamin B2, Niacin, Vitamin B6, Biotin, Choline, Vitamin B12 and Pantothenate.

17. A composition as set forth in claim 8, further comprising: one or more minerals selected from the group consisting of Sodium, Magnesium, Potassium, Calcium, Phosphate and Chloride.

18. A composition adapted to be used as a diet supplement solution for facilitating the adaptation of skeletal muscle and liver to a program of strenuous exercise, comprising: an amino acid mixture adapted to be added to every 400 milliliters of water used to make the solution, the amino acid mixture consisting essentially of 0.025 grams L-carnitine, 0.5 grams L-glutamine, 0.625 grams L-isoleucine, 0.85 grams L-leucine and 0.625 grams L-valine.

19. A composition as set forth in claim 18, further comprising: 2.5 grams of proteins adapted to be added to the water, the proteins being one or more selected from the group consisting of casein, soy protein and lactalbumin.

20. A composition as set forth in claim 18, further comprising: 25.0 grams of carbohydrates adapted to be added to the water, the carbohydrates being one or more selected from the group consisting of syrup solids and sucrose.

21. A composition as set forth in claim 18, further comprising: a fat mixture adapted to be added to the water, the fat mixture consisting essentially of 2.5 grams of a mixture of sunflower oil and soybean oil in a volumetric ratio of 1:1 and of 6.0 grams of medium-chain triglycerides.

22. A composition as set forth in claim 18, further comprising: a vitamin mixture adapted to be added to the water, the vitamin mixture consisting essentially of 6.0 mg. of Vitamin C, 35 microgram of Folic acid, 1.0 mg. Vitamin B1, 1.2 mg. Vitamin B2, 1.7 mg. of Niacin, 0.15 mg. Vitamin B6, 15 microgram of Biotin, 5.0 mg. of Choline, 1.0 microgram of Vitamin B12 and 0.2 mg. Pantothenate.

23. A composition as set forth in claim 18, further comprising: a mineral mixture adapted to be added to the water, the mineral mixture consisting essentially of 60 mg. of Sodium, 20 mg. of Magnesium, 200 mg. of Potassium, 50 mg. of Calcium, 75 mg. of Phosphate and 350 mg. of Chloride.

24. A composition as set forth in claim 18, further comprising: 2.5 grams of proteins adapted to be added to the water, the proteins being one or more selected from the group consisting of casein, soy protein and lactalbumin: 25.0 grams of carbohydrates adapted to be added to the water, the carbohydrates being one or more selected from the group consisting of syrup solids and sucrose; a fat mixture adapted to be added to the water, the fat mixture consisting essentially of 2.5 grams of a mixture of sunflower oil and soybean oil in a volumetric ratio of 1:1 and of 6.0 grams of medium-chain triglycerides; a vitamin mixture adapted to be added to the water, the vitamin mixture consisting essentially of 6.0 mg. of Vitamin C, 35 microgram of Folic acid, 1.0 mg. Vitamin B1, 1.2 mg. Vitamin B2, 1.7 mg. of Niacin, 0.15 mg. Vitamin B6, 15 microgram of Biotin, 5.0 mg. of Choline, 1.0 microgram of Vitamin B12 and 0.2 mg. Pantothenate; a mineral mixture adapted to be added to the water, the minerals mixture consisting essentially of 60 mg. of Sodium, 20 mg. of Magnesium, 200 mg. of Potassium, 50 mg. of Calcium, 75 mg. of Phosphate and 350 mg. of Chloride.

* * * * *

UNITED STATES PATENT AND TRADEMARK OFFICE
CERTIFICATE OF CORRECTION

PATENT NO. : 4,687,782
DATED : August 18, 1987
INVENTOR(S) : Eugene R. Brantman

It is certified that error appears in the above-identified patent and that said Letters Patent is hereby corrected as shown below:

Column 3, line 13, "$NH_4^3O$" should read -- $NH_4^+$ --.

Column 3, line 43, before "Further," insert --This BAA must derive from a net degradation of liver protein.--

Signed and Sealed this

Nineteenth Day of January, 1988

*Attest:*

DONALD J. QUIGG

*Attesting Officer*     *Commissioner of Patents and Trademarks*